United States Patent [19]

Grögler

[11] 4,259,255
[45] Mar. 31, 1981

[54] PROCESS FOR THE PRODUCTION OF ISOCYANATES

[75] Inventor: Gerhard Grögler, Leverkusen, Fed. Rep. of Germany

[73] Assignee: Bayer Aktiengesellschaft, Bayerwerk, Fed. Rep. of Germany

[21] Appl. No.: 15,577

[22] Filed: Feb. 26, 1979

Related U.S. Application Data

[63] Continuation of Ser. No. 821,017, Aug. 1, 1977, abandoned.

[30] Foreign Application Priority Data

Aug. 18, 1976 [DE] Fed. Rep. of Germany ....... 2637114

[51] Int. Cl.$^3$ .................. C07C 118/00; C07C 143/68
[52] U.S. Cl. ........................... 260/456 P; 260/453 P; 260/453 AR; 260/456 A; 544/221
[58] Field of Search .......... 260/453 P, 456 P, 453 AR

[56] References Cited

U.S. PATENT DOCUMENTS

| | | | |
|---|---|---|---|
| 3,404,170 | 10/1968 | Ulrich | 260/453 P |
| 3,580,942 | 5/1971 | Arlt | 260/453 P |
| 3,674,829 | 7/1972 | Arlt | 260/453 P X |
| 3,959,329 | 5/1976 | Dieterich et al. | 260/453 AR |

FOREIGN PATENT DOCUMENTS 485761 5/1938 United Kingdom .

*Primary Examiner*—Dolph H. Torrence
*Attorney, Agent, or Firm*—Gene Harsh; Joseph C. Gil; R. Brent Olson

[57] ABSTRACT

The instant invention relates to a process for the production of isocyanates in which tert.-alkyl urethanes are reacted with phosgene and to isocyanatoaryl sulphonic acid esters obtainable for the first time by this process.

6 Claims, No Drawings

PROCESS FOR THE PRODUCTION OF ISOCYANATES

This is a continuation of application Ser. No. 821,017 filed Aug. 1, 1977, abandonded.

BACKGROUND OF THE INVENTION

Chemical modification of organic isocyanates with the isocyanate group left intact is often complicated by the high reactivity and lability of the isocyanate group. For example, it is not possible to produce isocyanatoaryl sulphonic acid esters in the same way as sulphonic acid esters free from isocyanate groups, i.e. by reacting the corresponding chlorosulphonyl aryl isocyanates with alcoholates or phenolates. If the reaction is carried out in alcoholic medium, for example, the isocyanate groups would react to form urethanes while in the heterogeneous phase, the alcoholates or phenolates, which are well known trimerization catalysts, would promote trimerization of the isocyanate groups to form the corresponding isocyanurate derivative. One way of avoiding these reactions would be by blocking the isocyanate groups with known blocking agents for isocyanate groups before such a reaction. The isocyanate groups would be reformed by thermally splitting off the blocking agent after completion of the reaction leading to the sulphonic acid ester formation. However, such a process would probably result in considerable losses of yield on account of the considerable thermal stressing involved.

DESCRIPTION OF THE INVENTION

The present invention provides a new process which enables isocyanate groups which are blocked by tertiary alcohols to be liberated in particularly high yields. This method opens up a new way of producing certain substituted organic isocyanates.

The present invention therefore relates to a process for the production of organic isocyanates wherein compounds corresponding to the following general formula:

$R_1$—NH—CO—O—$R_2$ wherein $R_1$ represents an organic radical which optionally contains further substituents corresponding to the following general formula:

—NH—CO—O—$R_2$ but which is otherwise inert under the reaction conditions; and $R_2$ represents a radical of the type formed by removing the hydroxyl group from a tertiary alcohol;

are reacted with phosgene.

The process according to the present invention is particularly suitable for the production of a new class of compounds, namely isocyanatoaryl sulphonic acid esters.

Accordingly, the present invention also relates to isocyanatoaryl sulphonic acid esters.

Isocyanatoaryl sulphonic acid esters are extremely interesting compounds for the following reasons: First, the isocyanate group is able to enter into all the known addition reactions of isocyanate chemistry with active hydrogen low molecular weight and high molecular weight compounds (cf. Polyurethanes, Chemistry and Technology, part I, J. H. Saunders and K. C. Frisch, Interscience Publishers (1962)). One or more strongly alkylating sulphonic acid ester groups can thereby be introduced into mono- or poly-functional active hydrogen compounds or into the polyurethanes produced from them. Secondly, NCO-groups may additionally be incorporated by way of quarternizing reactions of the sulphonic acid ester group with suitable acceptors, such as one or more compounds containing tertiary nitrogen. In this case, modified isocyanates having ionic centers are obtained. Particularly in the high molecular weight range, this leads to end products having particularly desirable properties upon further polyaddition with H-active reactants. In addition, isocyanates containing an additional sulphonic acid group which have only weak, if any, alkylating activity (e.g. $R_1$ represents aryl) may be expected to have far more favorable physiological behavior than pure isocyanates. They would be expected to more quickly degrade in and be secreted from the body ("detoxicated isocyanates"). The same applies to polyaddition polymers synthesized from isocyanatoaryl sulphonic acid esters and the degradation products thereof.

The process according to the present invention represents a method of obtaining isocyanatoaryl sulphonic acid esters of the type in question. However, the process according to the present invention is not limited to the production of isocyanatoaryl sulphonic acid esters because it allows the recovery of isocyanates in high yields from organic isocyanates containing isocyanate groups masked by tertiary alcohols. This reaction permits to close the reaction chain from unmodified isocyanate with free isocyanate groups to unmodified isocyanate with blocked isocyanate groups and therefrom to modified isocyanate with blocked isocyanate groups and finally therefrom to modified isocyanate with free isocyanate groups. By this sequence of reaction steps any unmodified isocyanate may be modified with modification agents which are reactive with isocyanate groups but which are not reactive with isocyanate groups which are blocked with a tert. alcohol. Thus the chlorosulphonylarylisocyanates set forth hereinafter may be considered "unmodified isocyanates" which are modified with alcoholates or phenolates subsequent to the blocking reaction with tert. alcohols. Subsequent to the modification reaction the blocked isocyanate groups are converted into free isocyanate groups by reaction with phosgene. Without such preliminary blocking of the isocyanate groups these would have reacted under the influence of the alcoholates of phenolates i.e. under trimerisation.

Any organic mono- or poly-isocyanates containing isocyanate groups blocked by tertiary alcohols and containing substituents inert under the phosgenation reaction conditions, (apart from the blocked isocyanate groups), may be used in the process according to the present invention.

To carry out the process according to the present invention, the mono- or poly-isocyanate containing isocyanate groups blocked by tertiary alcohol are preferably reacted in solution in a suitable inert solvent, such as chlorobenzene, dichlorobenzene, nitrobenzene, benzonitrile or phenylacetic acid nitrile, with gaseous phosgene or with a solution of phosgene in one of the solvents exemplified above at temperatures of from 80° to 220° C., preferably from 120° to 170° C. The quantitative ratios between the reactants are preferably selected in such a way that at least one molecule of phosgene is available per blocked isocyanate group. The reaction mixture is then worked-up, preferably by distillation or recrystallization of the reaction product. In the reaction according to the present invention, a quantity of carbon dioxide equivalent to the quantity of phosgene reacted and a quantity of olefin equivalent to the blocked isocyanate used are formed in addition to the free isocyanate and hydrogen chloride. In cases where, for example, tertiary butanol is used as blocking agent, gaseous isobutylene is formed. Accordingly, the end of the reaction may readily be recognized by the end of the evolution of olefin and carbon dioxide.

In the particular case of the isocyanatoaryl sulphonic acid esters according to the present invention, the corresponding isocyanatoaryl sulphonic acid esters containing isocyanate groups blocked by tertiary alcohols are used as starting materials in the process of the present invention.

Basically, any compounds corresponding to the following general formula:

$$R_1-NH-CO-O-R_2$$

wherein $R_1$ and $R_2$ are as defined above; may be used for the process according to the present invention.

In the production of the isocyanatoaryl sulphonic acid esters according to the present invention, the starting materials used are compounds corresponding to the last of the above general formulae wherein $R_1$ represents an alkoxy-, cycloalkoxy- or aryloxy-sulphonyl-aryl-radical optionally substituted by $C_1$–$C_4$-alkyl groups, or optionally carrying oxygen atoms, sulphur atoms, sulphonyl-, carbonyl- or $C_1$–$C_5$-alkylene groups as bridge members and optionally substituted at the aryl group by further substituents of the formula —NH—CO—O—$R_2$ and wherein $R_2$ is as defined above.

The starting materials used for the production of the isocyanatoaryl sulphonic acid esters which are particularly preferred in accordance with the present invention are compounds corresponding to the following general formula:

$$(R_4O-SO_2)_n-R_3-(NH-CO-O-R_2')_m$$

wherein $R_2'$ represents the hydrocarbon radical of a tertiary aliphatic alcohol having from 4 to 10 carbon atoms;

$R_3$ represents an optionally $C_1$–$C_4$ alkyl-substituted (m+n)-functional aromatic hydrocarbon radical having from 6 to 15 carbon atoms;

$R_4$ represents an alkyl group having from 1 to 4 carbon atoms;

m represents 1 or 2; and n represents 1 or 2;

these compounds being reacted with phosgene.

The starting materials used for the production of the isocyanatoaryl sulphonic acid esters according to the present invention may be obtained from the corresponding aromatic amino sulphonic acids by known methods of preparative organic chemistry. For example, the preferred starting materials corresponding to the following general formula:

$$(R_4O-SO_2)_n-R_3-(NH-CO-O-R_2')_m$$

are prepared by reacting the aromatic amino sulphonic acid corresponding to the following general formula:

$$(HO-SO_2)_n-R_3-(NH_2)_m$$

in known manner with phosgene. The corresponding isocyanatoaryl sulphonic acid chloride corresponding to the following general formula:

$$(Cl-SO_2)_n-R_3-(NCO)_m$$

is thus formed. This phosgenation reaction is preferably carried out in the presence of suitable solvents, such as dichlorobenzene, at temperatures of from 150° to 180° C.

The isocyanato sulphonic acid chloride is then reacted with a tertiary alcohol corresponding to the following general formula:

$$HO-R_2'$$

to form the corresponding chlorosulphonyl-substituted urethane corresponding to the following general formula:

$$(Cl-SO_2)_n-R_3-(NH-CO-O-R_2')_m$$

This reaction is also preferably carried out in the presence of suitable solvents, such as dichlorobenzene, nitrobenzene, benzonitrile or phenyl acetic acid nitrile, at moderately elevated temperatures, for example from 20° to 50° C. The reaction mixture obtained may then be directly reacted, i.e. without further working-up, with alcoholates (or phenolates) corresponding to the following general formula:

$$Me-O-R_4$$

(wherein Me represents Na or K) optionally in the presence of the corresponding free alcohol ($R_4OH$) to form the starting material used in the process according to the present invention. After filtering off the precipitated sodium or potassium chloride and distilling off the $R_2OH$ or $R_4OH$ alcohol (which may be present in excess) at a temperature below 100° C., preferably at a temperature of from 40° to 60° C., the resulting product may then be used in the process according to the present invention.

By suitably selecting the starting materials (aminosulphonic acid, tertiary alcohol and alcoholate or phenolate), it is possible to produce any isocyanatoaryl sulphonic acid ester containing blocked isocyanate groups and in turn any isocyanatoaryl sulphonic acid ester.

Suitable aromatic aminosulphonic acids include, for example, 2-aminobenzene sulphonic acid; 5-chloro-2-aminobenzene sulphonic acid; 3-aminobenzene sulphonic acid; 4-aminobenzene sulphonic acid; 2,4-diaminobenzene sulphonic acid; 2,5-diaminobenzene sulphonic acid; 4-aminotoluene-2-sulphonic acid; 2-aminotoluene-4-sulphonic acid; 4,6-diaminotoluene-3-sulphonic acid; 6-aminotoluene-3-sulphonic acid; 5-chloro-6-aminotoluene-3-sulphonic acid; 2-aminotoluene-4-sulphonic acid; 2,6-diaminotoluene-4-sulphonic acid; 6-amino-1,3-dimethylbenzene-4-sulphonic acid; 4,6-diaminotoluene-3-sulphonic acid; 4-aminonaphthalene-1-sulphonic acid; 5-aminonaphthalene-1-sulphonic acid; 6-aminonaphthalene-1-sulphonic acid; 5-aminobenzene-1,3-disulphonic acid; 5-aminonaphthalene-1,3-disulphonic acid; 4,4'-diaminobiphenyl-2-sulphonic acid; 4,4'-diaminodiphenylether-2-sulphonic acid; 4,4'-diaminodiphenylsulphide-2,2'-disulphonic acid; 2-amino-1-phenoxybenzene-4-sulphonic acid; 2-amino-4'- methyldiphenylsulphone-4-sulphonic acid; 4,4'-diaminodiphenylmethane-2,2'-disulphonic acid and 4,4'-diaminodibenzyl-2,2'-disulphonic acid.

Suitable tertiary alcohols include, for example, tertiary butanol, 2-methyl-2-butanol, 2-methyl-2-pentanol, 3-methyl-3-pentanol, 3-ethyl-3-pentanol, 1-methylcyclohexanol, 1-ethylcyclohexanol, 1,1-dimethylallyl alcohol and 1,1-dimethylbenzyl alcohol. Tertiary butanol is preferred.

Suitable alcoholates or phenolates include, for example, sodium methylate, potassium methylate, sodium ethylate, potassium ethylate, sodium-n-butylate, sodium cyclohexanolate or sodium phenolate. The alcoholates are preferred to the phenolates because the alkylating activity of the compounds of the present invention is considerably weakened in the case of aromatic sulphonic acid ester groups.

The NCO-groups of the isocyanatoaryl sulphonic acid esters according to the present invention are strongly activated by the influence of the sulphonic acid ester groups. In addition, the sulphonic acid methyl, ethyl and propyl esters according to the present invention in particular show pronounced alkylating activity. Accordingly, the new compounds according to the present invention represent valuable starting materials for numerous organic syntheses. For example, isocyanatoaryl sulphonic acid esters may be trimerized by strong trimerization catalysts, such as sodium phenolate, to form the corresponding isocyanurate derivatives which contain at least three sulphonic acid ester groups per molecule (cf. Example 1). Monoisocyanatoaryl sulphonic acid esters are converted by the action of water into diphenyl urea disulphonic acid esters with vigorous evolution of $CO_2$ (Example 3). In both cases, interesting polyalkylating agents are formed. By reacting isocyanatoaryl sulphonic acid esters according to the present invention with, for example, polyhydroxyl compounds by the basic isocyanatepolyaddition reaction, it is possible to obtain polyurethanes having incorporated alkylating groups which may be reacted with diamines, for example, to form ionically cross-linked plastics having interesting properties.

The new isocyanatoaryl sulphonic acid esters may also be obtained by blocking the isocyanate groups of the corresponding chlorosulphonyl aryl isocyanates with phenols, esterifying the sulphochloride group with alcoholate and thermally splitting off the phenol used as blocking agent. Suitable phenols include, for example, phenol, chlorophenol, hydroxy toluenes, hydroxyethyl benzenes, hydroxydimethyl benzenes and nonylphenol. In cases where the phenols are used, just as in the above-described blocking of the isocyanate groups with tertiary alcohols, the equivalent quantity of blocking agent is added with stirring to the isocyanatoaryl sulphonic acid chloride in one of the above-mentioned high-boiling inert solvents. In this connection, it is advisable to accelerate the reaction using known catalysts for the isocyanate addition reaction, such as tin (II)ethylhexoate, dibutyl tin dilaurate, iron or zinc acetyl acetonate. The reaction temperature for blocking should, as far as possible, be in the range of from 40° to 60° C. to prevent inter-molecular sulphonation of the urethane aryl sulphochlorides. On completion of the blocking reaction, the blocked isocyanate may be crystallized out according to its solubility in the inert solvent, as is also the case where tertiary alcohols are used as the blocking agent. However, by adding the alcohol required for esterifying the sulphochloride group, the urethane precipitated may be quickly redissolved. Esterification is then carried out in the same way as described above with reference to the example of the intermediate products blocked by tertiary alcohol. After the solvent has been completely distilled off in vacuo (from 0.1 to 10 Torr), the oily or solid residue is subjected to pyrolysis. In general, the aromatic blocking agent is thermally split off in high vacuum (from 0.1 to 0.5 Torr) at temperatures of from 150° to 180° C. The lower boiling component is removed from the equilibrium by distillation. Thereafter, the residue may either be distilled or recrystallized. In this particular method of producing the isocyanatoaryl sulphonic acid esters of the present invention, it is generally not possible to obtain the high yields as with the process which uses tertiary alcohols as the blocking agent.

EXAMPLES

The production of the isocyanatoaryl sulphonic acid esters used in the process of the present invention using isocyanates blocked by tertiary alcohol, and also the further reaction thereof in accordance with Examples 1 to 7 below, is carried out in general as follows:

1.0 mol of tertiary alcohol is added dropwise over a period of about 30 minutes to a solution, heated to 30° C., of 1.0 mol of isocyanatoaryl sulphonic acid chloride: $(OCN)_m-R_3-(SO_2Cl)_n$ wherein n and m represent 1; in 0.5 to 1 liter of dichlorobenzene, nitrobenzene, benzonitrile or phenylacetic acid nitrile. After the exothermic reaction has abated, the reaction mixture is stirred for five hours at room temperature. A solution of 1.0 mol of sodium alcoholate in 250 ml of the corresponding alcohol is added to this reaction mixture over a period of one hour, the reaction temperature rising to from 30° to 40° C. The precipitation of NaCl takes place slowly, so that the reaction mixture is stirred for another five hours at room temperature. By adding 200 ml of ether, it is possible to accelerate the precipitation of NaCl or to promote its filtration. The alcohol still present is distilled off from the reaction solution, which is now free from NaCl, in vacuo (10 Torr) at from 50° to 60° C. The residual solution is phosgenated in known manner. The reaction is over after from 2 to 4 hours at a phosgenation temperature of from 150° to 170° C. Removal of the solvent by evaporation in vacuo (10 Torr) leaves behind the crude isocyanatoaryl sulphonic acid ester which may be further purified by distillation or recrystallization.

In Examples 1 to 7 tert.-butanol was used as the blocking agent.

The yields are based on the amount of isocyanatoaryl sulphonic acid chloride used.

EXAMPLE 1

| Starting compound = 4-isocyanatotoluene-2-sulphonic acid chloride | | | | |
|---|---|---|---|---|
|  | C | H | N | Cl | S |
| calculated: | 41.5 | 2.6 | 6.04 | 15.3 | 13.8 |
| observed: | 42.0 | 2.6 | 6.2 | 15.1 | 13.8 |

$Bp_{0.05}$: 122–125° C.; Mp.: 55–57° C.

Solvent = dichlorobenzene
Esterification = Na-methylate
4-isocyanatotoluene-2-sulphonic acid methyl ester

|  | C | H | N | S |
|---|---|---|---|---|
| calculated: | 47.57 | 4.0 | 6.2 | 14.1 |

-continued

| | | | | |
|---|---|---|---|---|
| observed: | 47.1 | 4.0 | 6.4 | 13.6 |

Bp$_{0.2}$: 158–164° C.; Yield: 78% of the theoretical yield

NCO determination reveals a content of from 19.0 to 19.5% (calculated 18.5%).

With strong trimerization catalysts, such as sodium phenolate, the isocyanatotoluene-2-sulphonic acid methyl ester may be trimerized into the corresponding isocyanurate derivative which then contains three strongly alkylating sulphonic acid methyl ester groups in the molecule.

| Mp: with decomposition | | | | |
|---|---|---|---|---|
| | C | H | N | S |
| calculated: | 47.6 | 3.9 | 6.2 | 14.10 |
| observed: | 47.3 | 3.3 | 6.1 | 13.9 |

EXAMPLE 2

If, instead of sodium methylate, sodium ethylate in solution in alcohol is used for esterifying the urethane toluene-2-sulphonic acid chloride according to Example 1, the 4-isocyanatotoluene-2-sulphonic acid ethyl ester is similarly obtained.

| | C | H | N | S |
|---|---|---|---|---|
| calculated: | 49.7 | 4.7 | 5.8 | 13.3 |
| observed: | 50.3 | 4.6 | 5.7 | 13.0 |

Above 180° C. decomposition occurs with evolution of gas.

EXAMPLE 3

Starting compound: 3-isocyanatobenzene sulphonic acid chloride
Solvent: benzonitrile
Esterification: Na-methylate
3-isocyanatobenzene sulphonic acid methyl ester

| | C | H | N | S |
|---|---|---|---|---|
| Calculated: | 45.0 | 3.3 | 6.56 | 15.0 |
| observed: | 45.0 | 3.3 | 6.6 | 14.8 |

Bp$_{0.05}$: 140–146° C.; Mp: 54–56° C.;
Yield: 80% (crude compound).

If 2 mols of 3-isocyanatobenzene sulphonic acid methyl ester in solution in acetone are reacted with 1 mol of $H_2O$, diphenylurea-3,3'-disulphonic acid methyl ester is obtained with vigorous evolution of $CO_2$.

| | C | H | N | S |
|---|---|---|---|---|
| calculated: | 44.8 | 4.0 | 6.97 | 15.9 |
| observed: | 45.4 | 4.2 | 7.1 | 15.3 |

Mp$_{(methanol)}$: 156–157° C.

EXAMPLE 4

Starting compound: 4-isocyanatobenzene sulphonic acid chloride
Solvent: dichlorobenzene
Esterification: Na-methylate
4-isocyanatobenzene sulphonic acid methyl ester

| | C | H | N | S |
|---|---|---|---|---|
| calculated: | 45.0 | 3.3 | 6.56 | 15.0 |
| observed: | 45.2 | 3.3 | 6.5 | 15.3 |

Bp$_{0.1}$ = 137–140° C.
Mp$_{(ether)}$ = 45–46° C., Yield 62% of the theoretical yield

EXAMPLE 5

Starting compound: 2,6-diisocyanatotoluene sulphonic acid chloride

| | C | H | N | S | Cl |
|---|---|---|---|---|---|
| calculated: | 39.7 | 1.8 | 10.3 | 11.8 | 13.1 |
| observed: | 40.3 | 2.0 | 10.1 | 11.6 | 13.6 |

Bp$_{0.2}$ = 152–156° C.
Mp$_{(ether)}$ = 46–50° C.

Solvent: phenylacetic acid nitrile
Esterification: Na-methylate
2,6-diisocyanatotoluene sulphonic acid methyl ester

| | C | H | N | S |
|---|---|---|---|---|
| calculated: | 44.8 | 3.0 | 10.5 | 11.95 |
| observed: | 45.0 | 3.2 | 10.4 | 11.6 |

Mp$_{(ether)}$: 79–80° C., Yield 58% of the theoretical yield

The NCO determinations carried out quickly at room temperature reveal an NCO content of 31.8% (calculated 31.4%).

EXAMPLE 6

Starting compound: 2,5-diisocyanatobenzene sulphonic acid chloride

| | C | H | N | S | Cl |
|---|---|---|---|---|---|
| calculated: | 37.1 | 1.2 | 10.8 | 12.4 | 13.7 |
| observed: | 37.9 | 1.2 | 10.9 | 12.2 | 13.9 |

Bp$_{0.1}$ = 146–150° C.
Mp$_{(ether)}$: 56–58° C.

Solvent: benzonitrile
Esterification: Na-methylate
2,5-diisocyanatobenzene sulphonic acid methyl ester

| | C | H | N | S |
|---|---|---|---|---|
| calculated: | 42.5 | 2.4 | 11.0 | 12.6 |
| observed: | 42.8 | 2.3 | 10.8 | 12.0 |

Bp$_{0.2}$: 155–160° C.
Mp: 60–62° C., Yield: 62% of the theoretical yield

EXAMPLE 7

Starting compound: 7-isocyanatonaphthalene-1-sulphonic acid chloride

| | C | H | N | S | Cl |
|---|---|---|---|---|---|
| calculated: | 49.3 | 2.2 | 5.2 | 11.96 | 13.3 |
| observed: | 49.7 | 2.5 | 5.2 | 11.8 | 13.0 |

Mp: 132–135° C.

Solvent phenylacetic acid nitrile
Esterification: Na-methylate

| 7-isocyanatoaphthalene-1-sulphonic acid methyl ester | | | | |
|---|---|---|---|---|
| | C | H | N | S |
| calculated: | 54.8 | 3.4 | 5.3 | 12.2 |
| observed: | 54.2 | 3.3 | 5.0 | 12.5 |
| Mp: 140–146° C., Yield: 45% of the theoretical yield | | | | |

EXAMPLE 8

A mixture of 94 g (1.0 mol) of phenol, 150 ml of dichlorobenzene and 0.3 g of tin(II)ethylhexoate is added at room temperature to a solution of 217.5 g (1.0 mol) of 3-isocyanatobenzene sulphonic acid chloride in 300 ml of dichlorobenzene. The reaction mixture is then heated for one hour to from 40° to 50° C. After cooling, 268 g (86% of the theoretical yield) of the phenyl urethane are gradually precipitated (Mp: 128°–130° C.).

140 g (0.45 mol) of the phenyl urethane are dissolved in 500 ml of methanol. A solution of 10.35 g (0.45 mol) of sodium in 200 ml of methanol is then added dropwise over a period of 30 minutes at room temperature, after which the reaction mixture is stirred for three hours. After about half the methanol has been distilled off and the NaCl precipitated has been filtered off, water is added to the filtrate, the urethane sulphonic acid methyl ester precipitating in the form of a colorless oil. Thermal splitting of the $H_2O$-free sulphonic acid methyl ester may be carried out under a pressure of from 1 to 2 Torr. The phenol which distills over at from 60° to 80° C. may readily be separated off and hence removed from the equilibrium. The required 3-isocyanatobenzene sulphonic acid methyl ester is then obtained at from 150° to 160° C. in a yield of 50% of the theoretical yield. Redistillation gives a colorless oil which immediately solidifies (Mp: 55°–57° C.).

| | C | H | N | S |
|---|---|---|---|---|
| calculated: | 45.0 | 3.3 | 6.6 | 15.0 |
| observed: | 45.4 | 3.7 | 6.7 | 15.0 |

What is claimed is:

1. A process for the production of organic isocyanates, comprising the steps of: (a) reacting an organic isocyanate with a tertiary alcohol thereby producing compounds corresponding to the following general formula:

$$R_1-NH-CO-O-R_2$$

wherein
 $R_1$ represents an inert organic radical which optionally may contain substituents corresponding to the general formula: $-NH-CO-O-R_2$; but which is otherwise inert under the reaction conditions; and
 $R_2$ represents a radical of the type formed by removing the hydroxyl group from a tertiary alcohol;
(b) reacting the product of step (a) with a material which is reactive with isocyanate groups but which is not reactive with isocyanate groups which are blocked with a tertiary alcohol; and (c) reacting the product of step (b) with phosgene.

2. The process of claim 1, wherein $R_1$ in the production of step (b) represents an alkoxy-, cycloalkoxy- or aryloxy-sulphonyl-aryl-radical optionally substituted by $C_1$–$C_4$-alkyl groups, or optionally carrying oxygen atoms, sulphur atoms, sulphonyl-, carbonyl- or $C_1$–$C_5$-alkylene groups as bridge members and optionally substituted at the aryl group by further substituents of the formula $-NH-CO-O-R_2$.

3. The process of claim 1 wherein the tertiary alcohol used in step (a) is tertiary butanol.

4. The process of claim 1 wherein the compound produced according to step (b) is of the formula:

$$(R_4O-SO_2)_nR_3-(NH-CO-O-R_2')_m$$

wherein
 $R_2'$ represents the hydrocarbon radical of a tertiary aliphatic alcohol having from 4 to 10 carbon atoms;
 $R_3$ represents an optionally $C_1$–$C_4$ alkyl-substituted (m+n)-functional aromatic hydrocarbon radical having from 6 to 15 carbon atoms;
 $R_4$ represents an alkyl group having from 1 to 4 carbon atoms;
 m represents 1 or 2; and
 n represents 1 or 2.

5. The process for the production of organic isocyanates comprising:
 (a) reacting
  (1) isocyanates of the general formula $$(Cl-SO_2)_n-R_3-(NCO)_m$$

wherein
 $R_3$ represents an optionally $C_1$–$C_4$ alkyl-substituted (m+n)-functional aromatic hydrocarbon radical having from 6 to 15 carbon atoms;
 m represents 1 or 2; and
 n represents 1 or 2 with
  (2) tertiary aliphatic alcohol having from 4 to 10 carbon atoms;
 (b) reacting the blocked isocyanate produced in step (a) with an alcoholate or phenolate; and
 (c) reacting the modified blocked isocyanate of step (b) with phosgene.

6. A process for the preparation of isocyanatoaryl sulfonic acid esters comprising
 (a) reacting (1) compounds corresponding to the formula $(Cl-SO_2)_n-R_3(NCO)_m$ with (2) phenol
wherein
 $R_3$ represents an optionally $C_1$–$C_4$ alkyl-substituted (m+n)-functional aromatic hydrocarbon radical having from 6 to 15 carbon atoms;
 m represents 1 or 2; and
 n represents 1 or 2;
 (b) esterifying the sulfochloride group of the product of step (a) with an alcoholate; and
 (c) thermally splitting off the phenol used as blocking agent.

* * * * *